(12) United States Patent
Musa

(10) Patent No.: US 6,706,835 B2
(45) Date of Patent: Mar. 16, 2004

(54) CURABLE COMPOSITIONS CONTAINING THIAZOLE FUNCTIONALITY

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 23 days.

(21) Appl. No.: 10/200,481

(22) Filed: Jul. 19, 2002

(65) Prior Publication Data

US 2004/0014903 A1 Jan. 22, 2004

(51) Int. Cl.[7] ............... C08F 122/38; C08F 122/40; C08G 59/44
(52) U.S. Cl. ............ 526/262; 526/264; 528/44; 528/45; 528/59; 528/117; 528/172; 528/211; 528/253
(58) Field of Search ............... 526/262, 264; 528/117, 172, 211, 253, 44, 45, 59

(56) References Cited

U.S. PATENT DOCUMENTS 6,300,456 B1 * 10/2001 Musa ............ 528/44
6,316,566 B1 * 11/2001 Ma et al. ........... 526/264
6,355,750 B1 * 3/2002 Herr ............ 526/262

OTHER PUBLICATIONS

Cerruti, Pierfrancesco et al.: "Synthesis and Characterization of Aromatic Poly(benzobisthiazole)s and Poly[oxy(bisbenzothiazole)]s Containing Flexible Linkages"; Macromol. Chem. Phys. 2002, 203, No. 3.; Wiley–VCH Verlag GmbH 69469 Weinheim 2002.

Samyn, Celest et al.: "Chromophore functionalised maleimide copolymers with high poling stabilities of the nonlinear optical effect at elevated temperature"; Polymer 42 (2001) 8511–8516.

Dang, Thuy D. et al.: "Aromatic Benzobisazole Polymers Containing 4–Hdroxypyridine–2,6–Diyl Unit"; Polymeric Materials: Science & Engineering 2001, 84, 467.

Weng, Jian et al.: "Synthesis and magnetic properties of novel poly(Schiff base)–$Fe^{2+}$ complexes"; Macromol. Rapid Commun. 2000, 21, 1099–1102, No. 15.; Wiley–VCH Verlag GmbH, D–69451 Weinheim 2000.

Weng, Jian et al.: "Syntheses and Magnetic Properties of Novel Bithiazole–Containing Polymeric Complexes"; Journal of Applied Polymer Science, vol. 81, 1353–1359 (2001); John Wiley & Sons, Inc.

Sun, Weilin et al.: "Synthesis and Properties of Poly–Schiff Base Containing Bisthiazole Rings"; Institute of Chemistry, Academia Sinica, Beijing 100080, People's Republic of China; 1997 John Wiley & Sons, Inc.

* cited by examiner

Primary Examiner—Robert Deshon Harlan
(74) Attorney, Agent, or Firm—Jane E. Gennaro

(57) ABSTRACT

Adhesion promoting compounds or resins containing a thiazole functionality (including benzothiazole) and a polymerizable functionality (Z) give improved adhesive strength to metal substrates. A representative structure is the following, in which $R^1$ and $R^2$ together can form a cyclic or aromatic structure, or are linear or branched organic moieties.

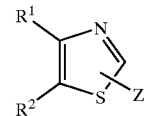

5 Claims, No Drawings

CURABLE COMPOSITIONS CONTAINING THIAZOLE FUNCTIONALITY

FIELD OF THE INVENTION

This invention relates to curable compositions containing a compound having a thiazole functionality and a polymerizable functionality.

BACKGROUND OF THE INVENTION

In the assembly of a semiconductor package to a printed wire boad, an integrated circuit chip is attached to a metal lead frame with adhesive and wire bonding, and the whole assembly then encapsulated in a molding resin. After encapsulation, the outer leads of the lead frame are attached to a printed circuit board. Any exposed copper surfaces on the lead frames or boards are subject to oxidation with exposure to air and routinely are coated with an antioxidant. Benzotriazole is an efficient corrosion inhibitor for copper and copper alloys in many environments. However, the presence of benzotriazole is suspected of interfering with the bonding process during the die attach, wire bonding, encapsulation, and final soldering operations in the manufacture of the semiconductor package and its attachment to a printed circuit board. Thus, there is a need for materials that will perform as a corrosion inhibitor and simultaneously promote adhesion.

SUMMARY OF THE INVENTION

This invention is a curable composition comprising a compound (hereinafter the thiazole compound) containing two chemistry segments: (1) a segment containing at least one thiazole functionality (including benzothiazole functionality), and (2) a segment containing at least one polymerizable functionality, such as, an electron donor functionality, an electron acceptor functionality, or an epoxy functionality.

DETAILED DESCRIPTION OF THE INVENTION

The thiazole functionality on the thiazole compound will have the following structure:

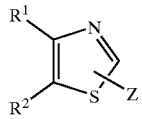

in which
  $R^1$ and $R^2$ independently are H or a linear or branched alkyl or alkylene group, or a substituted or unsubstituted cyclic alkyl or alkylene group, or a substituted or unsubstituted aromatic group;
  or $R^1$ and $R^2$ together form a substituted or unsubstituted cyclic alkyl or alkylene group;
  or $R^1$ and $R^2$ together form a substituted or unsubstituted aromatic or heteroaromatic ring or fused ring having 3 to 10 carbon atoms within the ring structure, in which the heteroatoms may be N, O, or S;
  in which the substituents on any ring are —$OR^3$, —$SR^3$, —$N(R^3)(R^4)$, or an alkyl or alkylene group having 1 to 12 carbon atoms, in which $R^3$ and $R^4$ independently are an alkyl or alkylene group having 1 to 12 carbon atoms, preferably 1 to 4 carbon atoms;
  and Z is any organic moiety that contains a polymerizable functionality.

Z can be polymeric, oligomeric, or monomeric, (for example, alkyl, cycloalkyl, aryl alkyl, alkenyl, cycloalkenyl, aryl alkenyl, or aromatic, and for example poly(butadiene), polyether, polyester, polyurethane, polyacrylic, polystyrene, polycarbonate, polysulfone).

The polymerizable functionality on Z will react with a complementary reactive functionality on any adhesive, coating, encapsulant, or other composition used in semiconductor manufacturing operations to immobilize the thiazole and prevent it from interfering with those manufacturing operations that are conducted proximate to metal surfaces.

Examples of polymerizable functionalities include electron donor groups, electron acceptor groups, and epoxy groups. Exemplary electron donor groups are vinyl ethers, vinyl silanes, compounds containing carbon to carbon double bonds attached to an aromatic ring and conjugated with the unsaturation in the aromatic ring, such as compounds derived from cinnamyl and styrenic starting compounds. Exemplary electron acceptor groups are acrylates, fumarates, maleates, and maleimides.

The thiazole compounds may be used as the main component of curable compositions, which will further comprise a curing agent and a filler.

Alternatively, the thiazole compounds of this invention may be added to adhesive, coating, encapsulant, or other curable compositions that come into contact with or that are required to bond to metal surfaces. As additives to retard oxidation and promote adhesion in curable compositions, they will be used in an effective amount to promote adhesion. In general, an effective amount will range from 0.005 to 20.0 percent by weight of the adhesive, coating, or encapsulant formulation.

In addition, such formulations will contain a polymerizable resin, optionally a curing initiator, and optionally a conductive or nonconductive filler.

Suitable polymerizable resins that may be used in the adhesive, coating, encapsulant or sealant formulations are known to practitioners in those arts. Examples of such resins include epoxies, electron donor resins, for example, vinyl ethers, vinyl silanes, and resins that contain carbon to carbon double bonds attached to an aromatic ring and conjugated with the unsaturation in the aromatic ring, such as compounds derived from cinnamyl and styrenic starting compounds; and electron acceptor resins, for example, fumarates, maleates, acrylates, maleimides, and thiol-enes (a compound resulting from the reaction of a thiol and a compound containing a carbon to carbon double bond).

Suitable curing agents are thermal initiators and photoinitiators present in an effective amount to cure the adhesive, coating, encapsulant or sealant formulation. In general, those amounts will range from 0.5% to 30%, preferably 1% to 20%, by weight of the total organic material (that is, excluding any inorganic fillers) in the formulation.

Preferred thermal initiators include peroxides, such as butyl peroctoates and dicumyl peroxide, and azo compounds, such as 2,2'-azobis (2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable: the curing process can be started either by irradiation, followed by heat, or can be started by heat, followed by irradiation.

In general, the formulations will cure within a temperature range of 70° C. to 250° C., and curing will be effected within a range of ten seconds to three hours. The actual cure profile will vary with the components and can be determined without undue experimentation by the practitioner.

The formulations may also comprise electrically or thermally conductive fillers or nonconductive fillers. Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. If present, fillers generally will be in amounts of 20% to 90% by weight of the formulation.

In another embodiment, the thiazole compounds may be used to coat on exposed metal surfaces, such as the copper surfaces of a semiconductor device or printed circuit board. The metal surface may first be degreased, cleaned, polished or buffed. In this embodiment, the thiazole adduct typically is used at a concentration of 0.5% to 20% in any suitable solvent. Representative suitable solvents are water, ketones (such as, methyl ethyl ketone, methyl isobutyl ketone, acetone), alcohols, glycol ethers, esters, and toluene.

The metal substrate is immersed in the solution for a period of time sufficient to deposit an effective coating. Immersion times typically will range from one second to one hour, more typically one minute to 15 minutes, although shorter or longer times may be effective depending on the particular thiazole compound, solution strength, and solution temperature. In general, the solution bath will be at a temperature within the range of 15° C. to 100° C.

Alternatively, the thiazole compound in solution can be sprayed or painted onto the metal surface to be coated. The solution is typically air-dried from the surface, and then cured at an elevated temperature suitable for removing any remaining solvent and for effecting curing.

SYNTHETIC PROCEDURES

The following procedures were used to prepare the thiazole compounds used in the EXAMPLES.

PROCEDURE 1: Reaction of alkyl halide with alcohol. One mole equivalent of alcohol, an excess amount of 50% NaOH, a catalytic amount of tetrabutyl ammonium hydrogen sulfate, and one mole equivalent of alkyl halide in toluene are stirred for five hours at 53° C., then five hours at 750° C. The reaction is allowed to cool to room temperature and the organic layer extracted and washed with brine three times. The isolated organic layer is then dried over $MgSO_4$, filtered, and the solvent removed in vacuo to give the product.

PROCEDURE 2: Reaction of alcohol with acid chloride. One mole equivalent each of alcohol and triethylamine are mixed in dry methylene chloride at 0° C. One mole equivalent acid chloride dissolved in dry methylene chloride is carefully added. The mixture is allowed to react for four hours. The solvent is evaporated and the crude product is purified by column chromato-graphy using a gradient of hexane/ethyl acetate to give the product.

EXAMPLE 1

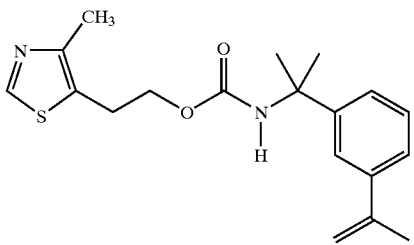

3-Isopropenyl-α,α-dimethylbenzyl isocyanate (m-TMI, 21.1 g, 0.105 mole) was solvated in 50 mL toluene in a 100 mL three-necked flask equipped with a mechanical stirrer, addition funnel and nitrogen inlet/outlet. The reaction was placed under nitrogen, and 0.01 equiv. dibutyltin dilaurate (catalyst) was added with stirring as the solution heated to 80° C. The addition funnel was charged with 5-(2-hydroxyethyl)-4-methylthiazole (15.0 g, 0.105 mole) dissolved in 50 mL toluene.

This solution was then added to the isocyanate solution over ten minutes, and the resulting mixture heated for an additional four hours at 80° C. After the reaction was allowed to cool to room temperature, the mixture was washed with distilled water three times. The isolated organic layer was then dried over $MgSO_4$, filtered, and the solvent removed in vacuo to give the product as a white solid in 97% yield.

EXAMPLE 2

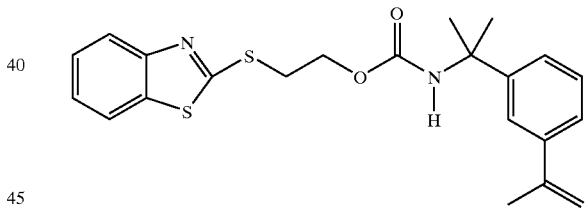

3-lsopropenyl-α,α-dimethylbenzyl isocyanate (m-TMI, 19.05 g, 0.095 mole) was solvated in 50 mL toluene in a 100 mL three-necked flask equipped with a mechanical stirrer, addition funnel and nitrogen inlet/outlet. The reaction was placed under nitrogen, and 0.01 equiv. dibutyltin dilaurate (catalyst) was added with stirring as the solution heated to 80° C. The addition funnel was charged with 2-(2-benzothiazolylthio)ethanol (20.0 g, 0.095 mole) dissolved in 50 mL toluene.

This solution was then added to the isocyanate solution over ten minutes, and the resulting mixture heated for an additional four hours at 80° C. After the reaction was allowed to cool to room temperature, the mixture was washed with distilled water three times. The isolated organic layer was then dried over $MgSb_4$, filtered, and the solvent removed in vacuo to give the product as a thick liquid (viscosity=4,000 cPs at 50° C.) in 95% yield.

EXAMPLE 3

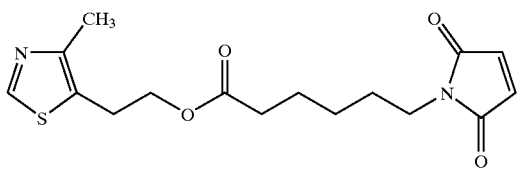

A solution of one mole equivalent of maleic anhydride in acetonitrile is added to a one mole equivalent of 6-aminocaprioc acid in acetic acid. The mixture is allowed to react for three hours at room temperature. The formed white crystals are filtered off, washed with cold acetonitrile and dried to produce the amic acid adduct. Amic acid is mixed with triethylamine in toluene. The mixture is heated to 130° C. for two hours and water is collected in Dean-Stark trap. The organic solvent is evaporated and the 2M HCL added to reach pH 2. Extraction with ethyl acetate and drying over $MgSO_4$ followed by evaporating the solvent gave 6-maleimidocaproic acid (MCA).

6-Maleimidocaproic acid (MCA, 45.13 g, 0.214 mole), 5-(2-hydroxyethyl) 4-methylthiazole (30.41 g, 0.214 mole) and 250 mL toluene were added to a 500 mL three-necked flask and heated to 80° C. in an oil bath until dissolved. Sulfuric acid catalyst (0.384 g) was added and heat was increased to 140° C. After 11 hours of heating, theoretical water (3.9 mL) was dropped along with 25 mL of toluene from Dean-Stark apparatus. Toluene, 25 mL, was replaced into the flask and the reaction was continued. This was done three additional times. Triethyl amine (10.80 mL) was added and the mixture was allowed to stir for one hour at room temperature. NaCl (20%) was added to the mixture and the mixture was transferred to a separatory funnel. The organic layer was isolated and dried over $MgSO_4$, followed by evaporating the solvent to give the product in 62% yield.

EXAMPLE 4

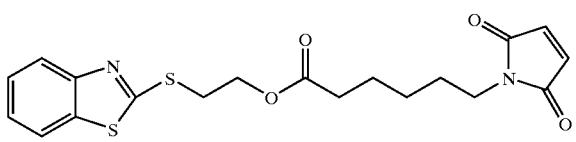

6-Maleimidocaproic acid (MCA, 45.13 g, one mole equivalent), 2-(2-benzothiazolylthio) ethanol (one mole equivalent) and toluene are added to a three-necked flask and heated to 80° C. in an oil bath until dissolved. Sulfuric acid catalyst (catalytic amount) is added and heat is increased to 140° C. After 11 hours of heating, theoretical water is dropped along with toluene from Dean-Stark apparatus. Toluene is replaced in the flask and the reaction continued. This is done three additional times. Triethyl amine is added and the mixture is allowed to stir for one hour at room temperature. NaCl (20%) is added to the mixture and the mixture is transferred to a separatory funnel. The organic layer is isolated and dried over $MgSO_4$, followed by evaporating the solvent to give the product.

EXAMPLE 5

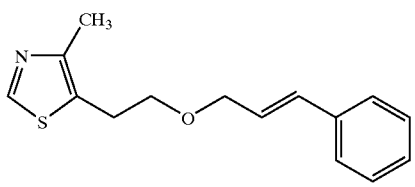

This thiazole compound is prepared according to PROCEDURE 1 by the reaction of 5-(2-hydroxyethyl)4-methylthiazole and cinnamyl chloride.

EXAMPLE 6

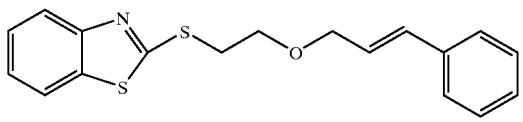

This thiazole compound is prepared according to PROCEDURE 1 by the reaction of 2-(2-benzothiazolylthio)ethanol and cinnamyl chloride.

EXAMPLE 7

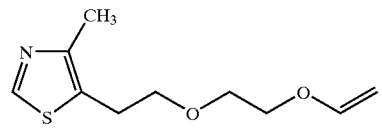

This thiazole compound is prepared according to PROCEDURE 1 by the reaction of 5-(2-hydroxyethyl)4-methylthiazole and 2-chloroethyl vinyl ether.

EXAMPLE 8

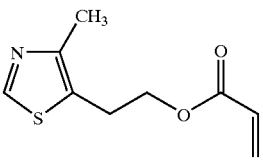

This thiazole compound is prepared according to PROCEDURE 2 by the reaction of 5-(2-hydroxyethyl)4-methylthiazole and acryloyl chloride.

EXAMPLE 9

The thiazole compound from EXAMPLE 1 was formulated into an adhesive composition and used to attach a 500×500 mil silicon semiconductor die to a copper leadframe with a 650×650 mil die pad. The adhesive composition contained a bismaleimide resin, a cinnamyl resin, a radical initiator, poly(butadiene) and silver filler, and was dispensed onto the leadframe. A silicon die was placed onto the adhesive, and the adhesive was cured on a hot plate ("snap cure") at 200° C. for one minute. Ten assemblies for each adhesive composition were prepared. The cured assemblies were subjected to 85° C./85% relative humidity for 48 hours, after which the die was sheared from the copper leadframe at 90 degrees with a Dage 2400-PC Die Shear Tester at 260° C. The average die shear strength of the ten assemblies was 38 Kg force. An acceptable die shear strength for this application within the industry is 10 to 15 Kg force indicating that the presence of the thiazole compound in the adhesive composition gives adhesive strength on metal substrates within the acceptable industrial range.

EXAMPLE 10

The thiazole compound from EXAMPLE 2 was made into a solution in toluene at a concentration of 1%–2% by weight. Ten copper leadframes were dipped into the solution, were air-dried, and cured for 30 minutes at 120° C. The leadframes (die pad, 650×650 mil) were used as the substrate for a silicon die, 500×500 mil. An adhesive formulation, comprising a bismaleimide resin, a cinnamyl resin, a radical initiator, poly(butadiene) and silver filler, was dispensed on each leadframe, a silicon die placed onto the adhesive, and the adhesive cured in an oven at 175° C. for 30 minutes. The cured assemblies were then subjected to 85° C./85% relative humidity for 48 hours, after which they were tested for peel strength.

The same procedure was performed substituting benzotriazole for the benzothiazoles. The assemblies coated with benzotriazole exhibited an average peel strength of 0.05N, compared with the assemblies coated with benzothiazole, which exhibited a peel strength of 1.05N, indicating that coating a metal substrate with the thiazol compound improves adhesive strength over the commonly used benzotriazole adhesion promoter.

What is claimed:

1. A compound containing a thiazole functionality and a polymerizable functionality having the structure:

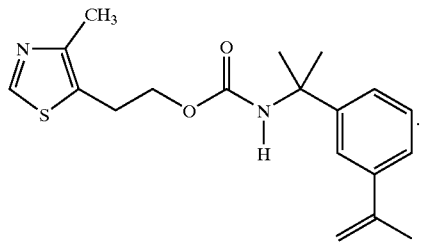

2. A compound containing a thiazole functionality and a polymerizable functionality having the structure:

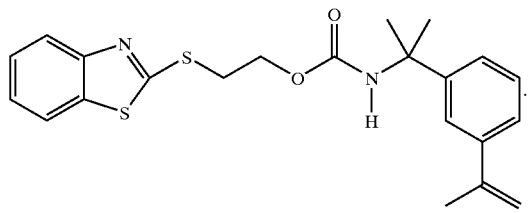

3. A compound containing a thiazole functionality and a polymerizable functionality having the structure:

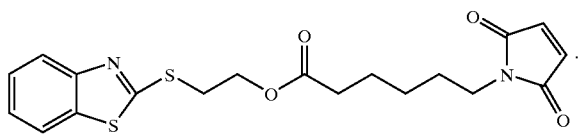

4. A curable composition comprising:

(a) a thiazole compound containing a thiazole functionality and a polymerizable functionality, the polymerizable functionality selected from the group consisting of electron donor, electron acceptor, or epoxy functionalities;

(b) a polymerizable resin;

(c) optionally, a curing agent; and (d) optionally, a filler.

5. The curable composition according to claim 4 in which the thiazole compound is selected from the group consisting of

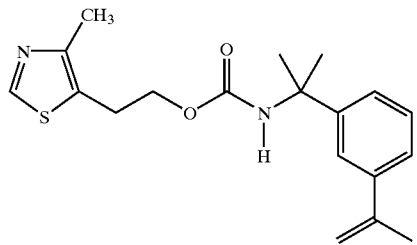

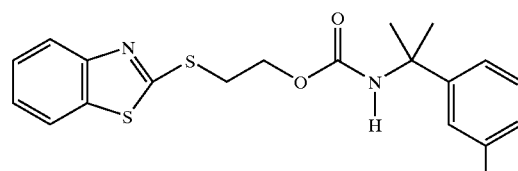

and

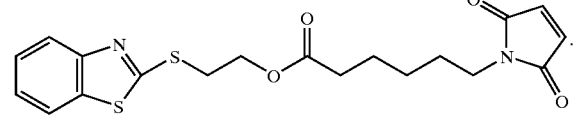

* * * * *